United States Patent [19]

Prescher et al.

[11] 4,048,225

[45] Sept. 13, 1977

[54] PROCESS FOR THE PRODUCTION OF PURE RACEMIC ACID AND MESOTARTARIC ACID

[75] Inventors: Günter Prescher; Gerd Schreyer, both of Hanau, Germany

[73] Assignee: Deutsche Gold- und Silber-Scheideanstalt vormals Roessler, Frankfurt, Germany

[21] Appl. No.: 660,789

[22] Filed: Feb. 24, 1976

[30] Foreign Application Priority Data

Sept. 29, 1975 Germany .............................. 2543333

[51] Int. Cl.² .............................................. C07C 59/14
[52] U.S. Cl. ................................................. 260/536
[58] Field of Search ......................................... 260/536

[56] References Cited

U.S. PATENT DOCUMENTS

| | | | |
|---|---|---|---|
| 2,437,648 | 3/1948 | Miles .................................... | 260/536 |
| 3,825,223 | 4/1975 | Yonemitsu et al. ................... | 260/536 |

FOREIGN PATENT DOCUMENTS

| | | | |
|---|---|---|---|
| 2,140,055 | 2/1973 | Germany ............................. | 260/536 |
| 1,183,449 | 3/1970 | United Kingdom ................. | 260/536 |

*Primary Examiner*—Paul J. Killos
*Attorney, Agent, or Firm*—Cushman, Darby & Cushman

[57] ABSTRACT

Pure racemic acid (dl-tartaric acid) and meso tartaric acid are produced by reaction of an alkali maleate with aqueous hydrogen peroxide in the presence of a catalyst which is an alkali molybdate or a mixture of an alkali molybdate and alkali tungstate in a process wherein the molar ratio of hydrogen peroxide to maleic acid is greater than 1:1 and the alkali salt of cis-epoxysuccinic acid formed together with the catalyst in a given case after destroying the excess hydrogen peroxide and other peroxygen compounds, are converted to free cis-epoxysuccinic acid and free molybdic acid or mixture of free molybdic acid and free tungstic acid by leading them over a strongly acidic cation exchanger, whereupon the hydrolysis of the free cis-epoxysuccinic acid to racemic acid and meso-tartaric acid can take place either in the presence of or the absence of the free molybdic acid or mixture of free molybdic acid and free tungstic acid, whereby the catalyst in the case of catalyst free hydrolysis before, and in the case of catalyst containing hydrolysis after this hydrolysis is removed with an anion exchanger and the racemic acid is then in known manner crystallized out of the catalyst free hydrolysis mixture by lowering the temperature in a given case with evaporation of water, whereupon the mesotartaric acid remains in the mother liquor, and there is recovered from the mother liquor either by crystallization or by evaporation to dryness, in a given case in admixture with racemic acid, unreacted cis-epoxysuccinic acid and maleic acid, while the anion exchanger laden with the molybdic acid or mixture of molybdic acid and tungstic acid is regenerated in known manner with dilute aqueous alkali and, in a given case, the resulting solution of alkali molybdate or mixture of alkali molybdate and alkali tungstate, eventually after treatment with activated carbon is returned directly into the epoxidation step.

30 Claims, No Drawings

PROCESS FOR THE PRODUCTION OF PURE RACEMIC ACID AND MESOTARTARIC ACID

The invention is directed to a process for the production of racemic acid (dl-tartaric acid) and mesotartaric acid by epoxidation of alkali salts of maleic acid with hydrogen peroxide in the presence of an alkali mloybdate or mixture of alkali molybdate and alkali tungstate in an aqueous medium at elevated temperature, conversion to the free acid and subsequent hydrolysis.

Several synthetic methods are known for the production of racemic acid (dl-tartaric acid) from maleic acid by the catalytic hydroxylation with hydrogen peroxide.

Thus free maleic acid is reacted in aqueous solution with hydrogen peroxide in the presence of alkali tungstates or molybdates, the intermediate epoxysuccinic acid formed hydrolyzed by boiling and then the racemic acid formed crystallized out of the hydrolysis solution, see Church and Blumberg, "Ind. Eng. Chem.", Vol. 43 (8) pages 1780 to 1786. The mother liquor of the racemic acid crystallization is again returned into the reaction step.

The return or working up of the mother liquor after the crystallization is of decisive significance for the industrial efficiency of the synthetic production of racemic acid, since it contains the added tungstate or molybdate catalyst and besides has a high portion of maleic acid, which cannot be thrown away. It is known to preferably so operate the pictured process that about 60% of the added maleic is reacted (loc. cit.).

The return of the resulting mother liquor, however, has great disadvantages since to begin with in its recycling impurities can become more concentrated which impair the quality of the racemic acid to be recovered.

On the other hand, it has been established that in the return of the mother liquor the speed of epoxidation is greatly reduced because of the saturation in tartaric acid, see Marechal German Offenlegungsschrift No. 2,016,668. The tartaric acid returned with the mother liquor besides is irreversibly oxidized in the epoxidation by hydrogen peroxide to worthless decomposition products such as formic acid, carbonic acid and water, see Marechal German Offenlegungsschrift No. 2,016,668.

To be sure according to the process of Marechal German O.S. No. 2,016,668 it was attempted to avoid a part of the described disadvantages by precipitating the tartaric acid in the mother liquor as the potassium or calcium salt before recycling the mother liquor.

It has been found, however, that the calcium salt is recovered in a form not completely free of catalyst, i.e. in the case of German O.S. No. 2,016,668 free of tungsten, entirely apart from the fact that the tartaric acid in part can only be recovered with difficulty from its salts. Also the tungsten catalyst after several processing cycles must be precipitated as the calcium salt and recovered therefrom because otherwise its activity subsides.

The racemic acid obtained according to the named process besides is not pure enough for food purposes.

If synthetic racemic acid is to be added in place of naural tartaric acid in the food sector there must be fulfilled very high purity requirements in regard to the content of malecic acid and fumaric acid as well as in regard to the content of traces of heavy metals, i.e., in regard to the catalyst content.

Since the described process operates partially with an excess of maleic acid (see Church and Blumberg, loc. cit. and German O.S. No. 2,016,668), the racemic acid must be crystallized from a maleic acid rich solution and is contaminated by adhering maleic acid, the more so the higher the yield that is crystallized out.

Besides under the reaction conditions maleic acid is partly rearranged to fumaric acid, which because of its lower solubility crystallizes out with the racemic acid. This contaminates the racemic acid and can only be separated therefrom with difficulty.

Consequently the resulting racemic acid in the known processes must be crystallized from solutions which still contain the total catalyst. Thereby a complete separation of the catalyst is not possible since it readily adheres to the crystallizing racemic acid and this is partially contaminated with coloration.

According to Wagner German O.S. No. 1,643,891 and the related Wagner U.S. Pat. No. 3,769,339, it is known to avoid a part of the described disadvantages by producing calcium tartrate by catalyzed reaction of the acidic calcium maleate with hydrogen peroxide. However, it is difficult to set free racemic acid from calcium tartrate, for example, by reaction with sulfuric acid as in the case with natural tartaric acid. The solubility products of the calcium sulfate and calcium tartrate resulting thereby are not sufficiently different so that losses occur through the tartrate content of the calcium sulfate or, in using an excess of sulfuric acid, the tartaric acid must be recovered from a sulfuric acid containing solution, which causes additional problems.

It was not known previously to produce mesotartaric from maleic acid and hydrogen peroxide, i.e., by way of cis-epoxysuccinic acid, but instead mesotartaric acid was recovered for example only in the hydrolysis of transepoxysuccinic acid, see Kuhn and Ebel, Berichte 58B, pages 919 et seq. (1925).

As catalysts for the epoxidation of unsaturated compounds there have already been proposed derivatives of numerous metals and semimetals, thus, e.g. tungsten, molybdenum, vanadium, chromium, selenium, osmium, titanium, zirconium, rhodium, uranium, ruthenium, tantallum, manganese and cobalt (see, e.g. the compilation in G. G. Allan, A. M. Neogi, J. of Catalysis, Volume 16, pages 197–203 (1970)).

According to previous knowledge, only tungstates or tungstic acid are considered the most effective catalysts in comparison to the compounds of the remaining metals, even in comparison to molybdic acid or molybdates (see M. Mugdam, D. P. Young, J. Chem. Soc. (1949), pages 2988 et seq; G. G. Allan, A. M. Neogi, loc. cit.).

In Kioustelidis German Auslegeschrift No. 2,140,055, it is established that substantially lower yields of racemic acid are produced with molybdic acid or molybdates than with tungstic acid or tungstates, but that in using tungstic acid or tungstates in the presence of acids there occur technical disturbances and catalyst losses. In order to avoid these disadvantages in the names Kioustelidis German A.S., there is employed a mixed catalyst of specified composition of molybdic acid and tungstic acid or molybdate and tungstate.

In German patent application P 25 08 228.4-42 and corresponding Prescher and Schreyer U.S. application 656,591, filed Feb. 9, 1976 entitled "Process for the Production of Pure Racemic Acid and Mesotartaric Acid and Separation of Maleic Acid from Synthetic Tartaric Acid" there is described a process for the production of pure racemic acid and meso-tartaric acid which avoids the described disadvantages using tungstates as catalyst. The entire disclosure of the Prescher et al U.S. application is hereby incorporated by reference and relied upon.

It would be of great industrial advantage if in place of the previously most effective known and highest yield producing tungstate catalyst there could be used the same process with molybdic acid or molybdate.

Since molybdic acid and its salts are cheaper than the corresponding tungsten compounds, loss of the expensive catalyst does not have as strong an economic effect.

Besides the carrying out of the process of German patent application P 25 08 228.4-42 and related Prescher et al United States application is more flexible through the addition of a catalyst different from the tungsten catalyst.

According to the situation the process can be adapted to the most favorable catalyst available, even a mixed catalyst with tungstic acid, namely in any customary mixing ratio of the two.

Entirely on the contrary it would be of high advantage for the industrial practicability of a tartaric acid process if customary mixing ratios of tungstate or molybdate catalysts could be employed without disadvantages in regard to the yield of the process, since then, for example the catalyst loss at the moment in time could be replaced both with tungstate or molybdate according to which catalyst was available at the moment.

It has now been found that racemic acid can be recovered in a continuously or discontinously operated process in higher yields and in very pure condition in addition to mesotartaric acid in the reaction of alkali metal maleate with aqueous hydrogen peroxide in the presence of a catalyst if the molar ratio of hydrogen peroxide to maleic acid is greater than 1:1 and the reaction is catalyzed by alkali molybdate or a mixture of alkali molybdate and alkali tungstate in any mole ratio to each other, whereupon the alkali salt of cis-epoxysuccinic acid formed together with the alkali salt of the catalyst, in a given case after destroying the excess hydrogen peroxide, are converted to free cis-epoxysuccinic acid and free molybdic acid or a mixture of free molybdic acid and free tungstic acid by leading them over a strongly acidic cation exchanger, e.g., a strong cation exchange resin, whereupon the hydrolysis of the free cis-epoxysuccinic acid to racemic acid and mesotartaric acid can take place either in the presence or the absence of the free molybdic acid or mixture of free molybdic acid and free tungstic acid, whereby the catalyst in the case of catalyst free hydrolysis before, and in the case of catalyst containing hydrolysis after this hydrolysis is removed with an anion exchanger, e.g., an anion exchanger resin, and the racemic acid is then in known manner crystallized out of the tungstic acid free hydrolysis mixture by lowering the temperature, in a given case by evaporation of water, whereupon the mesotartaric acid remains in the mother liquor and there is recovered from the mother liquor either by crystallization or evaporation to dryness, in a given case in admixture with racemic acid, unreacted cis-epoxysuccinic acid and maleic acid, while the anion exchanger laden with the molybdic acid or mixture of molybdic acid and tungstic acid is regenerated in known manner with dilute aqueous alkali and, in a given case, the resulting solution of alkali molybdate or mixture of alkali molybdate and alkali tungstate, eventually after treatment with activated carbon is returned directly into the epoxidation.

According to the process of the invention, dl-tartaric acid is industrially crystallized out of a solution which is practically free from catalyst acid and, to an extraordinarily small residue, is free from maleic acid and can therefrom be recovered from this solution in food grade purity.

Also, it was observed that in the hydrolysis of the cis-epoxysuccinic acid mesotartaric acid was formed, and it was found that its portion is influenced by the manner of carrying out the hydrolysis, i.e., by the presence or absence of the molybdate catalyst or mixed catalyst which can consist of any ratio of molybdic acid to tungstic acid.

The object of the invention is attained by the combination of the individual steps of the invention, i.e., proceeding from the salts of the maleic acid, which are reacted with excess hydrogen peroxide in the presence of molybdate or molybdate-tungstate catalyst, by way of the recovery of the free cis-epoxysuccinic acid and free molybdic acid or mixture of free molybdic acid and free tungstic acid with cation exchangers, as well as the described types of the hydrolysis and the removal of the catalyst acid by anion exchangers, the working up of the solution through fractional crystallization, dl-tartaric acid of high purity is produced and the resulting mesotartaric acid is recovered.

The catalyst is recovered very simply and practically quantitatively and without cumbersome working up returned directly in aqueous solution into the epoxidation step.

Furthermore, the process of the invention is easy to carry out industrially since up to the crystallization of the tartaric acid working is only with aqueous solutions and the known difficult manipulations of solids are completely avoided.

Added to this according to the process of the invention these advantages are attained with the molybdate catalyst generally considered disadvantageous to the yield, namely either alone or in any mixture with tungstate.

As alkali maleates or alkali molybdates/tungstates, there can be used the sodium, potassium and ammonium compounds, preferably the sodium compounds. (As used herein, the term alkali includes the Group Ia metals and ammonium.) The amounts of alkali maleate added are so regulated that the reaction runs in homogeneous medium during the entire duration of the reaction. Preferably in using sodium maleate the reaction solution should contain 10 to 20 wt.% maleic acid.

The ratio of hydrogen peroxide to maleic acid added should be between 1.01 to 5:1, preferably between 1.1 to 2:1. Especially favorable is a ratio of 1.1 to 1.3:1. The starting concentration of the aqueous $H_2O_2$ solution is immaterial. Thereby the excess of hydrogen peroxide should be so regulated that even with the decomposition losses of hydrogen peroxide there is always present during the entire reaction an excess of hydrogen peroxide in relation to maleic acid.

The reaction is usually carried out at pH values between 3 and 5.5, preferably at pH values of 4 to 5 and at temperatures of 70° to 90° C., although higher temperatures up to the boiling limit of the aqueous solution and lower temperatures down to the solubility limit of the maleate added or the epoxysuccinate formed by the raction can be used.

The catalyst, i.e., the alkali molybdate, e.g. sodium molybdate, potassium molybdate or ammonium molybdate or the sum of molybdate and tungstate, e.g., sodium tungstate, potassium tungstate or ammonium tungstate, can be used in amounts of 0.5 to 5 mol %, preferably 1 to 2 mol %, based on the maleic acid employed.

Thereby the reaction of the sodium salts of maleic acid with hydrogen peroxide in the presence of sodium molybdate or sodium tungstate to the sodium salts of the cis-epoxysuccinic acid is also known in itself, see Payne et al, J. Org. Chem., Vol. 24 (1959), pages 54 et seq., however, their change corresponding to the further steps of the process of the invention to produce tartaric acid are new.

The alkali maleate according to the process of the invention can be added either in preformed form or can be formed in situ in the reactor, and as starting material there can be used either maleic acid or maleic anhydride.

After the epoxidation reaction, the hydrogen peroxide and other peroxygen compounds such as pertungstates or permolybdates in a given case if necessary are removed. For removal of the peroxygen compounds there can be called upon both known chemical reactions as well as the known metal catalyzed decomposition of these compounds. Advantageously one works so that the solution is not contaminated and uses a catalyst which contains platinum on a solid carrier, for example, 0.01 to 5 weight % platinum on chemically inert low pore carriers which consist of more than 90% $SiO_2$, preferably 0.05 to 0.5 weight % platinum. With these catalysts, the peroxygen compounds in the solutions in question can be destroyed at normal pressure at temperatures of 20°–100° C., preferably at 60°–80° C.

Epoxidation and peroxide decomposition thereby can be carried out either continuously or discontinuously, according to which is suitable in each individual case. Thus the epoxidation can be carried out either batchwise in a stirred kettle or continuously in two or more successive loop reactors (recycling reactors or circulatory reactors) with subsequent flow tube according to German patent application P 25 08 228.4-42 and the corresponding Prescher and Schreyer United States application mentioned above. Likewise the decomposition of the excess peroxide can occur by leading the reacted epoxidation solution through a column filled with the decomposition catalyst or by allowing the catalyst to act discontinuously in a container, in a given case while stirring the liquid.

To recover the free cis-epoxysuccinic acid there can be used as strongly acidic cation exchangers all of the commercial types, especially those based on polystyrene or styrene-divinylbenzene copolymers having acid groups, preferably free sulfonic acid groups, attached thereto. Thus there can be used any of the particulate strongly acidic cation exchange resins in the Encyclopedia of Polymer Science and Technology, Vol. 7, pages 692–742. The entire disclosure of said pages is hereby incorporated by reference and relied upon.

For the process of the invention, it is immaterial whether there are employed known parallel flow, countercurrent flow or continuous ion-exchange processes. However, it is advantageous, without the process being limited thereby, to carry out the regeneration of the cation exchange resin countercurrently to the loading. Therethrough there are obtained the known advantages of countercurrent processes such as less alkali slippage (slippage = residual content of alkali in the exchanged solution) and less requirement of regeneration agent and therewith its higher economy is utilized. Particularly favorable are processes in which there are avoided the too strong dilution of the exchanged solution by the wash water accumulating in the course of the regeneration, since this dilution water additionally must be evaporated in the later working up, see, e.g., German patent application P 25 08 228.4-42 and the corresponding Prescher and Schreyer United States application mentioned above. Thereto there can also be used, for example, the method for setting free the epoxysuccinic acid from its alkali salt in the German patent application and the Prescher and Schreyer United States application without the process being limited thereby.

For this purpose, three cation exchangers are employed, of which two are connected in succession while the third is found in the regeneration. The cation exchanger in this form of the invention is washed with concentrated wash water from an earlier cycle.

As concentrated wash water there is designated a solution which results from the washing free from the product after the exhaustion of the cation exchanger, again see German patent application P 25 08 228.4-42 and the related Prescher and Schreyer United States application.

The first cation exchanger is preferably operated until breakthrough of alkali.

The aqueous solution of epoxysuccinic acid and molybdic acid or molybdic acid/tungstic acid after the cation exchanger, which solution also contains small amounts of unreacted maleic acid and small amounts of tartaric acid is then reacted at temperatures of 50°–200° C., preferably at temperatures of 100°–150° C. to form tartaric acid.

Thereby the reaction can also be carried out either discontinuously, for example, by boiling for several hours under reflux in a stirred vessel or continuously by leading the mixture through a reaction tube.

Hereby one can proceed in such manner that the aqueous solution resulting after the cation exchanger either is directly conveyed to the hydrolysis or one can so proceed that this solution first is led over one or more anion exchangers which are found in the hydroxyl or tartrate form and then is conveyed in catalyst free form to the hydrolysis.

The hydrolysis of aqueous cis-epoxysuccinic acid solutions is known in itself, see R. Kuhn and F. Ebel, Ber. 58B, 919 et seq. (1925); G. Wode, Svensk Kem. Tids., Vol. 40, pages 221 et seq. (1928) and Chem. Abst., Vol. 23 (1929) page 2344 as well as Yonemitsu, German Offenlegungsschrift No. 2,400,767.

Also here it was established that the portion of unexpectedly formed mesotartaric acid in the hydrolysis of the cis-epoxysuccinic acid is dependent on whether the hydrolysis is carried out before or after the anion exchange. (German application P 25 08 228.4-42 and the corresponding Prescher and Schreyer United States application.) This is the more surprising since according to R. Kuhn et al (loc. cit.) and Yonemitsu German O.S. No. 2,400,767 in the hydrolysis of an aqueous solution of cis-epoxysuccinic acid, as that resulting after the anion exchanger in the process of the invention, only d,l-tartaric acid forms. However, according to the process of the invention it was found that the portion of meso-tartaric acid formed can be reduced considerably if the hydrolysis is carried out in the presence of 0.1–5 mol %, preferably 1–2 mol %, of molybdic acid or the sum of molybdic acid and tungstic acid based on the cis-epoxysuccinic acid, i.e., before the anion exchange, in this regard see the subsequent examples.

It is also possible according to the process of the invention to so regulate the conditions according to demand that more or less mesotartaric acid is formed. Depending on demand also there can be obtained more or less dl-tartaric acid and in cases in which dl-tartaric is not in demand or has insufficient demand it can be replaced or supplemented by meso-tartaric acid.

For example this is the case if the solubility of the dl-tartaric acid is not adequate for the determined purposes of use. Since dl-tartaric acid differs from natural tartaric acid in its substantially poorer solubility while the solubility of mesotartaric acid is in the neighborhood of natural tartaric acid, then a solution with a higher portion of mesotartaric acid can also always be produced if the solubility of dl-tartaric acid is not sufficient for the concerned purpose in an industrial region of use, as for example in the construction industry or in the electroplating industry.

The introduction of anion exchangers for the removal of molybdate or tungstate containing compounds, even in the presence of polybasic complex forming acids, such as citric acid is known in itself (see, D. Shishkov, E. Koleva, Doklady, Bolg. Akad. Nauk. Vol. 17(10) pages 909–912 (1964) and Chemische Zentralblatt (1966) 27–538).

As anion exchangers there can be employed all commercial types, preferably weakly basic anion exchangers based on polystyrene or styrene-divinyl benzene copolymer with a macroporous structure and an amino function as the exchange active groups. Thus there can be used the particulate anion exchange resins mentioned in the aforecited Encyclopedia of Polymer Science and Technology, Vol. 7, pages 692–742. Also there can be used the anion exchange resins mentioned in Kioustelidis German O.S. No. 2,140,055 such as Amberlite IR 4B and Duolite A7, for example.

In the here described process of the invention it is immaterial whether the anion exchange is carried out according to a known parallel flow, countercurrent flow or continuous ion exchange process.

For quasi-continuous carrying out of the process one can operate for example as described in German patent application P 25 08 228.4-42 and the corresponding Prescher and Schreyer United States application by employing three columns of which two are connected in succession while the third is found in the regeneration whereby the first of the columns preferably is always operated up to breakthrough of the catalyst.

For the in principle success of the process, however, it is also sufficient to only use one column whereby the loading is interrupted shortly before the breakthrough of molybdate or tungstate and the resin regenerated. Before the regeneration of the resin preferably first the column content is displace with distilled water and together with fresh solution in the next loading again passed over the anion exchanger. The anion exchange beds are then regenerated, as is recommended by the resin manufacturer, with dilute aqueous alkali, e.g., sodium hydroxide, and subsequently the anion exchanger, likewise as recommended by the resin manufacturer, is washed free of alkali with deionized water. The regenerate combined with the wash waters contains, in a given case besides small amounts of the acids (or their salts) occurring in the solution added to the exchanger, the molybdate or the molybdatetungstate catalyst which can be returned practically quantitatively as a dilute, aqueous solution into the epoxidation step. Thereby it is necessary to install at least so much anion exchange resin that from the capacity of the installed resin the regeneration and washing of the anion exchanger column need only take place so infrequently that the amount of water brought in with the wash water and the dilute aqueous sodium hydroxide and returned to the epoxidation can be reused in the production of the epoxidation charge or, in continuous flow in the solutions led to the reactors.

Preferably before reintroduction of the regenerate into the epoxidation it is treated with activated carbon, since occasionally in the continuous running of the process yellow brown impurities are adsorbed on the anion exchanger. These reach the regenerate in the regeneration of the resin and contaminate the regenerate.

One can proceed in the purification so that 0.05–1 wt. %, preferably 0.1–0.4 wt. % of activated carbon based on the solution is stirred in, preferably at room temperature.

After a time of 5 minutes to 5 hours the activated carbon is filtered off and the completely uncolored solution used again. In place of room temperature higher or lower temperatures also can be employed, besides other processes can be used in place of the stirring in process, for example column processes in which the colored solution is led over an activated carbon tower.

The solution present after hydrolysis and anion exchange, which is practically free from catalyst, and besides small amounts of unreacted or on the anion exchange resin not separated maleic acid or traces of fumaric acid, contains the total dl-tartaric acid as well as a corresponding portion of mesotartaric acid and, in a given case, unreacted epoxysuccinic acid, can then be worked up, see Church and Blumberg, loc. cit. In a given case after evaporation of water the solution is cooled, the racemic acid filtered off and washed with cold water and subsequently dried.

The mesotartaric acid can thereby, for example after evaporation to dryness, be recovered in admixture with non-crystallized racemic acid and the residue of maleic acid and cis-epoxysuccinic acid.

The evaporation is best carried out at temperatures between 40° and 150° C., preferably 60°–110° C. and the crystallization at temperatures of 1°–25° C.

In order to produce particularly pure racemic acid, the solution is best fractionally crystallized.

For this purpose first a portion of the water is distilled off under vacuum, normal pressure or pressure.

This amount of water is adjusted according to the concentration of the solution of racemic acid, mesotartaric acid, cis-epoxysuccinic acid and maleic acid coming from the anion exchanger and according to the degree of purity of the racemic acid which it is desired to produce. The concentrated solution is led to a crystallization and filtration stage so that first crystallized racemic acid can be recovered and the aqueous mother liquor (called Mula I below) can be recovered.

The thus obtained Mula I can now again be evaporated in a corresponding manner to a further racemic acid fraction which can have a lesser purity according to the solubility and concentration of the remaining constituents. The number of fractions thereby is selectable at random. However, it is convenient to crystallize in not more than 2–4 fractions and to evaporate the final mother liquor to dryness.

In the working up of the last mother liquor, it has been found that it best contains the least possible cis-epoxysuccinic acid, since this crystallizes poorly and inclines to stick and thus make difficult the working up.

Since, however, even at high reaction during the hydrolysis of 98-99 %, cis-epoxysuccinic acid clearly concentrates in the mother liquor, it is industrially particularly advantageous to operate the evaporation under conditions in which the hydrolysis of the epoxysuccinic acid is continued to avoid too long reaction times in the true hydrolysis.

Advantageously for example a mother liquor can also undergo a subsequent saponification since in this place the total volume of the solution is clearly lower than in the true hydrolysis and so a smaller container is necessary.

The technical advantage of the invention, as already said, is first in the recovery of racemic acid which is very pure in reference to maleic acid, fumaric acid and impurities from the catalyst.

According to the "Deutschen Arzneimittelbuch 7" (German Medicine Book 7) for natural tartaric acid there is permitted a maximum heavy metal content (calculated as lead) of 20 ppm. The catalyst content of the dl-tartaric acid obtained according to the process of the invention is less than 5 ppm. According to the American Food Chemical Codex of 1966 malic acid included in the food grade range and produced from maleic acid is allowed to contain, maximally 0.05 wt. % maleic acid and 0.7 wt. % fumaric acid.

The dl-tartaric acid recovered by the process of the invention already contains less than 0.02 wt. % of maleic acid and fumaric acid and has therefore food grade purity.

Beside the process of the invention, as previously stated, is easy to carry out industrially, since up to the crystallization of the tartaric acid one is only working with aqueous solutions. The recovered catalyst can besides be returned immediately into the reaction step.

As already said, the process of the invention works with particular advantage with the cheap molybdenum catalyst which in other processes is clearly disadvantageous in regard to yield or with any mixture of molybdate and tungstate as catalyst, which increases the industrial flexibility of the process. Usually the amount of tungstate is not over 90% of the total molybdate and tungstate by weight, whereas it is possible to use amounts of tungstate up to 100%.

Unless other indicated, all parts and percentages are by weight.

The invention will be explained further in connection with the following examples.

EXAMPLE 1

There were dissolved 1,019.8 grams (10.4 moles) of maleic anhydride at 80° C. in an aqueous sodium alkaline solution in a stirred container. The solution contained 21.45 grams (0.104 mole) of sodium molybdate, 500 grams of NaOH and 4963 grams of water besides small amounts of organic acids which entered the regenerate in the regeneration of the anion exchanger.

The molybdate containing solution was prepared based on the molybdate content by using molybdate solution from the regenerate of the anion exchanger (see below) and adding this to the stated NaOH and water content.

The contents of the stirred containers were then brought to a pH of 4.5 with 40 wt. % aqueous sodium hydroxide. Subsequently at 80° C. there were dropped in as quickly as possible 870 grams of 50 wt. % hydrogen peroxide. Thereby the pH was held at 4.5 by addition of 40 wt. % sodium hydroxide until in all 622 grams of 40 wt. % aqueous sodium hydroxide were added. After the end of the $H_2O_2$ addition the charge was stirred for another 5 hours at 80° C. The maleic acid reaction then was 99.8%.

There were then added at 80° C. with stirring of the solution 200 ml of a contact catalyst which contained 0.1% platinum on a chemically inert low pore carrier which contained more than 90 wt. % of silicon dioxide and whose particle size was between 3-5 mm.

After 5 hours at 80° C., the residual peroxygen content was less than 0.01 wt. %. The solution, after being separated from the catalyst, was pumped with a velocity of 4 liters/hour at about 40° C. from below over two successively connected ion exchange columns (diameter 10 cm) each of which was filled with 11 liters of a strongly acid cation exchange resin, based on styrene-divinyl benzene copolymer having free sulfonic acid groups (® Lewatit S100F, Bayer Leverhusen).

In the swollen condition, the resin filled 95% of the free space between 2 sieve plates and was brought into the H+ form from above according to the instructions of the resin producer and was washed free of acid. Before the loading the resin was coated with water. After the loading, the contents of the ion exchange columns were displaced from below with completely salt free water. With rejection of the practically acid free portion of the solution which was obtained at the beginning there were obtained 20.7 liters of an aqueous product solution which was boiled under reflux for 5 hours. The solution contained 0.104 mole of molybdic acid, 0.021 mole of maleic acid, 0.2 mole epoxysuccinic acid, 0.698 mole of meso-tartaric and 9.27 mole of D,L-tartaric acid. The selectivity of the racemic acid based on the tartaric acid formed was also 93%, the meso-tartaric was 7%.

The solution was concentrated to an acid concentration of 1.37 val=equivalents/liter and led from below over a macroporous weakly basic, monofunctional anion exchanger (® Lewatit MP62 GA, Bayer Leverhusen) which after regeneration with aqueous sodium hydroxide (see below) was now filled with the same solution of product from an earlier loading.

There were charged into a 25 mm diameter column 310 ml of resin, loading was at about 22° C. according to the suspended bed technique with a velocity of 1-1.5 liters/hour.

There were obtained 14.8 liters of a solution which contained less than 2 ppm of molybdenum, 1392 grams of D,L-tartaric acid, 104 grams of meso-tartaric acid, about 26 grams of epoxysuccinic acid and about 1.2 grams of maleic acid. It was then evaporated (at about 50° C.) to an acid concentration of 3.5 val/1000 grams, cooled to about 5° C. and crystallized. The crystallized racemic acid was filtered off and carefully washed twice with 15 weight % of cold water, based on the solid product. There were obtained after drying 944 grams of D,L-tartaric acid (60.5% based on the maleic anhydride) with a molybdenum content of less than 2 ppm and a maleic acid and fumaric acid content of less than 0.02%.

After evaporation of the mother liquor to 3.6 val/1000 grams of acid, crystallization and washing, as described, there were obtained after drying 355 grams of D,L-tartaric acid (22.7% based on the maleic anhydride added), which contained less than 5 ppm of molybdenum, about 0.03% maleic acid and less than 0.02% fumaric acid.

The meso-tartaric acid fraction of 104 grams meso-tartaric acid, 93 grams of D,L-tartaric acid, 26 grams of epoxysuccinic acid and about 1.2 grams of maleic acid — this is all together 14.6% based on the maleic anhydride added — can be recovered by evaporation to dryness. The mixture is industrially valuable as such; however, it can also be purified through further fractional crystallization and the racemic acid separated more completely.

In the following there is described the regeneration of the anion exchanger, which was laden with 2 charges of the stated size.

First from above it was washed free of product with 1200 ml of completely salt free water; the solution was again charged for the next loading (there was present in this solution 1.7% of the molybdenum added.

Subsequently, the anion exchange resin was regenerated from above according to the instructions of the resin manufacturer with 1200 ml of 6 wt. % aqueous sodium hydroxide and washed alkali free with 1800 ml of completely salt free water. There was obtained a solution with 42.1 grams of $Na_2MoO_4$, small amounts of organic acids and sodium hydroxide; the solution contained 98.2% of the added (2 charges) $Na_2MoO_4$.

Together with the amount of 1.7% of the charge returned in the washing there were recovered 99.9% of the total charge.

The yellow colored regenerate was stirred for 30 minutes at room temperature with 0.4 weight % of activated carbon, based on the solution, and then filtered. The nearly decolored solution was added to the next reaction charged. It was supplemented with 1530 ml, containing 21.45 grams of sodium molybdate, to a content of 500 grams of NaOH and 4963 grams of water.

EXAMPLE 2

In order to improve the reaction in reference to epoxysuccinic acid a subsequent hydrolysis of the mother liquor of the second crystallization is carried out as shown in the following example.

One liter of mother liquor of the second crystallization according to example 1 was boiled in a glass flask for 5 hours under reflux. The solution contained 0.92 mol/1000 g of a mixture of dibasic acids which was composed of 0.7 mol % maleic acid, 40.8 mol % racemic acid, 45.6 mol % mesotartaric acid and 12.9% epoxysuccinic acid. After 5 hours of subsequent hydrolysis the solution contained 0.7 mol % maleic acid, 48.5 mol % racemic acid, 47.2 mol % mesotartaric acid, and about 3.6 mol % epoxysuccinic acid.

The reaction in the subsequent hydrolysis based on epoxysuccinic acid amounted to 72% whereby additional racemic acid and mesotartaric acid were formed.

EXAMPLE 3

A solution which was obtained according to example 1 after the cation exchanger was not hydrolyzed, but first was led over an anion exchanger, as is generally described in example 1.

The solution contained 0.756 mol/1000 g of a mixture of dibasic acids, namely 22 mol % of D,L-tartaric acid, 2 mol % meso-tartaric acid and 76 mol % epoxysuccinic acid. The molybdenum content of the solution was below 2 ppm (not detectable). After hydrolysis at 100° C. there resulted, based on the starting content of epoxysuccinic acid and tartaric acid, the following product distribution.

| Minutes | Mol % dl-tartaric Acid | Mol % Mesotartaric Acid | Mol % Epoxysuccinic Acid | Selectivity of Mesotartaric Acid Related to the Formed Tartaric Acid |
|---|---|---|---|---|
| 0 | 22 | 2 | 76 | 8.3 |
| 60 | 39 | 7 | 54 | 15.2 |
| 120 | 54 | 10 | 36 | 15.6 |
| 300 | 73 | 17 | 10 | 18.9 |

According to the process described in example 1 there was attained a selectivity of 7% mesotartaric acid based on the tartaric acid formed at a 98% reaction of epoxysuccinic acid. The analysis data obtained in example 3 was determined with the help of the nuclear resonance method.

By the procedure set forth in this example, the portion of meso-tartaric acid can be increased or by the method set forth in example 1 be reduced.

The process can comprise, consist essentially of or consist of the steps set forth using the stated materials.

What is claimed is:

1. A process for the production of pure racemic acid and mesotartaric acid comprising reacting an alkali maleate with aqueous hydrogen peroxide in a molar ratio of hydrogen peroxide to maleate of greater than 1:1 and also in the presence of (1) an alkali molybdate or (2) a mixture of an alkali molybdate and an alkali tungstate as a catalyst to form the alkali metal salt of cis-epoxysuccinic acid in solution, passing the reaction solution thus formed over a strongly acidic cation exchanger to form free cis-epoxysuccinic acid and free (1) molybdic acid or (2) a mixture of free molybdic acid and free tungstic acid, hydrolyzing the free cis-epoxysuccinic acid to form a hydrolysis mixture containing racemic acid and mesotartaric acid, removing the (1) molybdic acid or (2) mixture of molybdic acid and tungstic acid with an anion exchanger, crystallizing out the racemic acid from the (1) molybdic acid or (2) mixture of molybdic acid and tungstic acid free hydrolysis mixture by lowering the temperature of said hydrolysis mixture while retaining the mesotartaric acid in the mother liquor remaining after crystallization of the racemic acid and recovering the mesotartaric acid from the mother liquor.

2. The process of claim 1 including the step of regenerating the anion exchanger laden with (1) molybdic acid or (2) a mixture of molybdic acid and tungstic acid with dilute aqueous alkali and returning the resulting solution of (1) alkali molybdate or (2) mixture of alkali molybdate and alkali tungstate to serve again as catalyst in forming the alkali metal salt of cis-epoxysuccinic acid.

3. The process of claim 2 including the step of treating the (1) alkali molybdate or (2) mixture of alkali molybdate and alkali tungstate solution formed in the regeneration of the anion exchanger with activated carbon to remove color-forming impurities therein.

4. The process of claim 1 comprising destroying excess hydrogen peroxide and other peroxgen compounds prior to forming the free cis-epoxysuccinic acid.

5. The process of claim 1 comprising carrying out the hydrolysis of the cis-epoxysuccinic acid in the presence of (1) molybdic acid or (2) a mixture of molybdic acid and tungstic acid and removing the catalyst acid after the hydrolysis by passing the acid solution over an anion exchanger.

6. The process of claim 1 comprising removing (1) the molybdic acid or (2) the mixture of molybdic acid and tungstic acid by passing the epoxysuccinic acid solution over an anion exchanger prior to the hydrolysis.

7. The process of claim 1 comprising aiding the crystallization of the racemic acid by evaporating a portion of the water.

8. The process of claim 1 comprising recovering the mesotartaric acid from the mother liquor by crystallization.

9. The process of claim 1 comprising recovering the mesotartaric acid from the mother liquor by evaporating said liquor to dryness.

10. The process of claim 1 wherein the molar ratio of hydrogen peroxide to maleic acid employed is between 1.01:1 and 5:1.

11. The process of claim 10 wherein the ratio of hydrogen peroxide to maleic acid is between 1.1:1 and 2:1.

12. The process of claim 11 wherein the ratio of hydrogen peroxide to maleic acid is between 1.1:1 and 1.3:1.

13. The process of claim 1 comprising destroying the excess hydrogen peroxide and other peroxygen compounds prior to forming the free cis-epoxysuccinic acid by passing the hydrogen peroxide and other peroxygen compounds containing reaction solution over a low porosity carrier catalyst consisting essentially of more than 90 wt. % $SiO_2$ containing 0.01–5 wt. % Pt at a temperature of 20°–100° C.

14. The process of claim 1 wherein the strongly acidic cation exchanger is a water insoluble sulfonated styrene polymer.

15. The process of claim 1 wherein the cation exchanger is a sulfonated styrene-divinyl benzene copolymer and is arranged in a plurality of beds said process comprising passing the reaction solution through at least two of said beds in succession.

16. The process of claim 1 comprising regenerating the cation exchanger with concentrated wash water from a previous cycle.

17. The process of claim 1 comprising recovering the racemic acid from the solution subsequent to the anion exchanger by fractional crystallization.

18. The process of claim 1 wherein the anion exchanger is a weakly basic ion exchange resin.

19. The process of claim 18 wherein the anion exchange resin is a water insoluble aminated styrene polymer.

20. The process of claim 19 wherein the anion exchange resin is an aminated styrene-divinyl benzene copolymer.

21. The process of claim 1 wherein there are employed two cation exchange columns in succession and two anion exchange columns in succession, said process comprising operating the first cation exchange column until break through of alkali while the second cation exchange column is maintained substantially fresh and then replacing said first cation exchange column, operating the first anion exchange column until break through of acid while the second anion exchange column is maintained substantially fresh and then replacing said first anion exchange column.

22. The process of claim 1 comprising saponifying the mother liquor after the crystallization of the racemic acid.

23. The process of claim 1 wherein the catalyst solution obtained is purified by passing through activitated carbon and is then reused.

24. A process according to claim 1 wherein the catalyst is (1).

25. A process according to claim 24 wherein the molar ratio of hydrogen peroxide to maleic acid employed is between 1.01:1 and 5:1.

26. A process according to claim 1 wherein the catalyst is (2).

27. The process of claim 1 comprising carrying out the reaction of alkali maleate with hydrogen peroxide in a loop reactor.

28. The process of claim 27 comprising carrying out the reaction of alkali maleate with hydrogen peroxide in two or more than two loop reactors in succession.

29. The process of claim 1 comprising carrying out the reaction of alkali maleate with hydrogen peroxide in two loop reactors in succession and in a subsequent flow tube.

30. The process of claim 1 wherein the catalyst is a mixture of an alkali molybdate and an alkali tungstate, the amount of tungstate being not over 90% of the total molybdate and tungstate by weight.

* * * * *